United States Patent [19]

Yamazato et al.

[11] Patent Number: 5,221,626
[45] Date of Patent: Jun. 22, 1993

[54] COLORIMETRICALLY MEASURING METHOD OF ZINC

[75] Inventors: Fujio Yamazato, Tokyo; Kuniaki Tokuda, Saitama, both of Japan

[73] Assignee: Wako Pure Chemical Industries Ltd., Osaka, Japan

[21] Appl. No.: 590,552

[22] Filed: Sep. 26, 1990

Related U.S. Application Data

[63] Continuation of Ser. No. 171,122, Mar. 21, 1988, abandoned, which is a continuation of Ser. No. 897,274, Aug. 18, 1986, abandoned, which is a continuation of Ser. No. 676,283, Nov. 29, 1984, abandoned.

[30] Foreign Application Priority Data

Dec. 2, 1983 [JP] Japan .............................. 58-228221

[51] Int. Cl.$^5$ ............................................. G01N 33/20
[52] U.S. Cl. ........................................ 436/74; 436/81; 436/84; 436/166
[58] Field of Search ....................... 436/74, 84, 73, 81, 436/166; 252/408.1

[56] References Cited

U.S. PATENT DOCUMENTS 4,407,962 10/1983 Tabacco et al. ...................... 436/74

FOREIGN PATENT DOCUMENTS 3131698 3/1983 Fed. Rep. of Germany ........ 436/84
57-91975 6/1982 Japan .
59-30061 2/1984 Japan .

OTHER PUBLICATIONS

Chemical Abstracts, vol. 101, No. 17, Oct. 22, 1984, p. 353, No. 147313s.
Chemical Abstracts, vol. 90, No. 6, Feb. 5, 1979, p. 601, No. 47864h.
Chemical Abstracts, vol 99, No. 2, Jul. 11, 1983, p. 634, No. 15732h.
Chemical Abstracts, vol. 97, No. 6, Aug. 9, 1982, p. 650, No. 48790n.
Chemical Abstracts, vol. 87, No. 26, Dec. 1977, p. 181, No. 204734y.
Dolindo Laboratories Catalog Kangun-Machi, Kumamoto 862, Japan pp. 81 & 82.
The Merck Index, 10th Edition (1983), p. 473.
Makino et al, A highly sensitive colorimetric determination of serum zinc using water-soluble pyridylazo dye, 120 *Clinica Chemica Acta* 127 (1982).
Ujije et al, A New Micromethod For Colorimetric Determination of Zinc In Serum, 87 *Clinica Chimica Acta* 71 (1978).
Macka et al.: "Spectrophotometric Study of the Acid--Base and Optical Properties of the 5-Bromo and 5--Chloro Derivatives of 2-(2-Pyridylazo)-5-(Diethylamino) Phenol (BrPADAP, ClPADAP) and Their Complexation Equilibria with Zinc (II) Ions", *Coll. Czech. Chem. Commun.* 47 (10) 2676 (1982).
Industrial & Engineering Chemistry, vol. 11, No. 7 pp. 365-367 (1939), Ayres et al.
Chemical Abstract, vol. 99, p. 666 (1983), Wang et al.
Chemical Abstract, vol. 98, p. 400 (1983), Kuban et al.
Inorganic Anal. Chem. vol. 95, (1981) Chen et al.
Chemical Abstract, vol. 95, p. 752 (1981), Lin et al.
Inorganic Anal. Chem. vol. 76, 1972, Guser et al.
Chemical Abstract, vol. 98, p. 672 (1983), Deng et al.
Chemical Abstract, vol. 80, p. 534 (1974), Sbibata et al.
Chemical Abstract, vol. 101, p. 365 (1984), Zhe

*Primary Examiner*—Virginia Manoharan
*Attorney, Agent, or Firm*—Cushman, Darby & Cushman

[57] ABSTRACT

A method for the colorimetic determination of zinc including the steps of:
a) preparing a coloring reagent for zinc including
  1) an aqueous soluble 2-pyridylazoaminophenol derivative or a salt of a 2-pyridylazoaminophenol derivative, represented by the following formula (I):

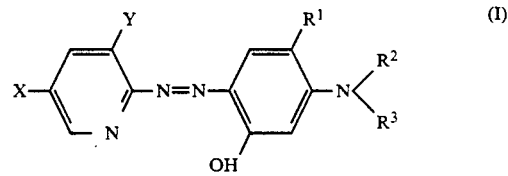

wherein
2) at least one surface active agent
3) a masking agent for a metal,
b) adding the coloring reagent solution to a sample solution containing zinc and
c) measuring the absorbance of the solution at 555 nm.

14 Claims, No Drawings

COLORIMETRICALLY MEASURING METHOD OF ZINC

This is a continuation of application Ser. No. 07/171,122, filed on Mar. 21, 1988, now abandoned, which is a continuation of Ser. No. 06/897,274, filed Aug. 18, 1986, abandoned, which is a continuation of 06/676,283, filed Nov. 29, 1984, abandoned.

BACKGROUND OF THE INVENTION (1) Field of the Invention

The present invention relates to a novel method of colorimetrically measuring zinc.

(2) Description of the Prior Art

Recently, the quantitative measurement of a small amount of a metal rises in importance with respect to environmental sanitation and biochemical diagnosis method. In particular, zinc is a metal present in a small amount in the living organisms and one of the indispensable metal elements necessary for the growth, and is widely distributed in the bodies of the living organisms. It has been lately reported that the concentration of zinc in serum lowers in positive acrodermatitis, taste impediment, SLE (systemic lupus erythematosus), zinc deficiency symptom observed in the case of administration of a high calorie transfusion, and so on, and the necessity of the measurement of the zinc in serum has been felt in the diagnosis, treatment and prognosis of these diseases.

As the method of quantitatively measuring a small amount of zinc until today, the atomic absorption method, the flame photometric method, and the colorimetrically measuring method are mainly used, and the colorimetrically measuring method is advantageous from the standpoint that a number of specimens to be examined can be promptly treated and no special analysing device is necessary.

As the colorimetric reagent, use may be mainly made of dithizone, zincon, PAN{1-(2-pyridylazo)-2-naphthol}, but any one of them is not necessarily complete from the viewpoint of specificity. In order to remove the interference of iron, copper, cobalt and manganese, it was necessary to use a cyano compound or a variety of masking agents in combination or use an extraction with an organic solvent.

Under the circumstances, the present inventors have noted the compounds disclosed in Japanese Patent Application Laid-Open No. 91,975,1982 which have been developed as a high sensitivity colorimetrically measuring reagents for a small amount of a metal and have a molecular absorption coefficient of $7.0-13.3 \times 10^{-4}$. Although these compounds are all useful as the high sensitivity colorimetrically measuring reagents for the heavy metal, they have the defect that they sense a small amount of a metal other than zinc in the case of pyridylazophenol compounds like in the pyridylazonaphtol compounds because their general non-specificity.

Accordingly, when the above compounds are used, metals other than the intended specific ones are required to be masked as conventionally done.

For this purpose, use have generally been made of citrates, condensed phosphate, sodium fluoride, and nitrilotriacetic acid, 1-hydroxyethane-1,1-diphosphonic acid for the masking agents of iron; salicylaldoxime, 2-mercaptobenzothiazol, dithiocarboxyzarcosine, and dithiocarboxy glycine for the masking agents of copper; and dithiocarboxyzarcosine, and 2-mercaptobenzothiazol for the masking agents of cobalt.

Thus, they are very inconvenient in that some of these masking agents mask the intended zinc to lower the sensitivity thereof (for instance, citric acid, condensed phosphoric acid), and substances containing a partial structure —S—C=S or and —SH group, which are used as the masking agents of copper and cobalt, are conspicuously poor in stability after the preparation thereof, and these substances may be a coloring promotor of iron because they reduce trivalent iron to divalent iron.

SUMMARY OF THE INVENTION

It is therefore an object of the present invention to provide a method of colorimetrically measuring zinc using a masking agent which is excellent in stability and specifically acts upon specific metal.

It is another object of the present invention to provide a method of colorimetrically measuring zinc at a high sensitivity.

That is, according to the present invention, the method of colorimetrically measuring zinc using as a coloring reagent a 2-pyridylazoaminophenol derivative represented by the general formula (I):

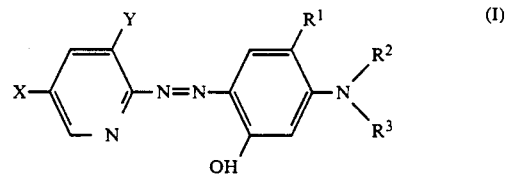

wherein X and Y represents a halogen atom or a hydrogen atom, $R^1$ represents a hydrogen atom or a lower alkyl group, and $R^2$ and $R^3$ represents a hydrogen atom, a lower alkyl group, —$(CH_2)_nSO_3H$ in which n is an integer or 1-4,

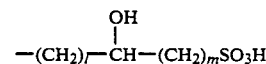

in which l is an integer of 0-4 and m is an integer of 0-4, or a salt thereof, is characterized in that one or more kinds of surface active agents are used as a masking agent.

These and other objects, features and advantages of the invention will be well appreciated upon reading of the following description with understanding that some modifications, variations and changes could be easily done by the skilled in the art to which the invention pertains without departing from the spirit of the invention nor the scope of the claims appended thereto.

DETAILED DESCRIPTION OF THE INVENTION

The present inventors have strenuously made various studies and examinations on a method of colorimetrically measuring zinc using as a coloring reagent 2-pyridylazoaminophenol derivative represented by the following formula (I):

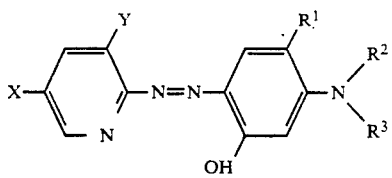

in which X and Y represent a halogen atom or a hydrogen atom, $R^1$ represents a hydrogen atom or a lower alkyl group, and $R^2$ and $R^3$ represent a hydrogen atom, a lower alkyl group, $-(CH_2)_n SO_3H$ in which n is an integer of 1-4, or

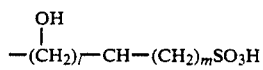

in which l is an integer of 0-4 and m is an integer of 0-4, or a salt thereof, and found that a surface active agent exhibits a great effect as a masking agent of a specific metal, so that they have accomplished the present invention.

That is, the present invention relates to a method of colorimetrically measuring zinc by using a 2-pyridylazoaminophenol derivative represented by the general formula (I) or the salt thereof as a coloring reagent, wherein one or more kinds of surface active agents are used as a masking agent.

The surface active agents are used in the colorimetrically analyzing methods as a solubilizing agent of coloring reagents hard to dissolve, and for the purpose of shifting of absorption wavelength and prevention of turbidity of a sample, clarification of the sample, stabilization of color development, isolation of the intended metal from the metal combined protein or so, extraction of produced chelate into an organic solvent. The present inventors have found that the surface active agents can be used for the purpose quite different from the above-mentioned ones that is, they can act as the masking agent of the metals and have accomplished the invention.

The surface active agents used in the present invention are not specifically restricted, and those that clarifically dissolve in a range of pH 4-10 which is appropriate for the coloring reagent are preferred.

Particularly nonionic, cationic and an amphoteric surface active agent are preferable because they do not interfere the coloring of zinc, and inhibits the coloring of iron, copper, cobalt and nickel. Further similar effects can be obtained when the anionic surface active agent and the nonionic surface active agent are used in combination. When these surface active agents are used together with the conventional masking agent, the effects of the above-mentioned surface active agents are remarkably increased.

As the nonionic surface active agents particularly effective for the present invention, use may be made of Triton X-100 (polyoxyethylene iso-octylphenyl ether, Rohm & Haas Co., Ltd., trade name) Brij-35(polyoxyethylene lauryl ether, Kao Atlas Co. Ltd., trade name), Emulgen 120(polyoxyethylene lauryl ether, Kao Atlas Co. Ltd., trade name), Tween 20 (polyoxyethylenesorbitan monolauryl ether, Kao Atlas Co. Ltd., trade name), Tween 80 (polyoxyethylene sorbitan monooleyl ether, Kao Atlas Co. Ltd., trade name), Softanol 90 (polyoxyethylene alkyl ether, Nippon Catalyst Chemical Industries Ltd), Triton X-405 (polyoxyethylene, Rohm & Haas Co., Ltd., trade name), Emulgen 147 (polyoxyethylene lauryl ether, Kao Atlas Co., Ltd., trade name), Emulgen 920 (polyoxyethylene lauryl ether, Kao Atlas Co., Ltd., trade name), Emulgen 950 (polyoxyethylene nonylphenyl ether, Kao Atlas Co., Ltd., trade name), Emulgen PP 290 N(oxyethyleneoxypropylene block polymer, Kao Atlas Co., Ltd., trade name), Emusol 3130 (polyoxyethylenesorbitanemonostearate, Kao Atlas Co., Ltd., trade name) and so on, but the present invention is not restricted to the above-mentioned ones.

As to the anionic surface active agents, use may be made of Sundet EMN (polyethylenealkyl ether sulfuric acid ester sodium salt, Sanyo Kasei Kogyo Co., Ltd., trade name), Emarl NC (polyoxyethylenealkylphenyl ether sulfuric acid ester, Kao Atlas Co., Ltd., trade name), Aranon ACE (N-cocopyl-N-methyl-$\beta$-alanine sodium salt, Kawaken Fine Chemical Co., Ltd., trade name), Emarl 20 C (polyoxyethylene alkylsulfate sodium salt, Kao Atlas Co., Ltd., trade name), Nonipol S-40 (polyethylene alkylphenyl ether sulfuric acid ester sodium salt, Sanyo Kasei Kogyo Co., Ltd., trade name), sodium lauryl sulfate (sodium salt of lauryl sulfuric acid ester), Sundet BL (alkylbenzene sulfonic acid formalin condensate, Sanyo Kasei Kogyo Co., Ltd., trade name), Levenol WX (polyoxyethylenealkyl sulfate sodium salt, Kao Atlas Co., Ltd., trade name), Ultrafon W (pentadecylbenzimidazol sulfonic acid sodium salt, Nippon CIBA-GEIGY Co., Ltd., trade name), Demol N (naphthalene sulfonic acid formalin condensate, Kao Atlas, Co., Ltd., trade name), Softanol 30S-25( secondary alkyl sulfuric acid sodium salt, Nippon Catalyst Chemical Industries, Ltd., trade name), Levenol WZ (polyoxyethylenealkyl sulfate sodium salt, Kao Atlas Co., Ltd., tradename) and the like, but the present invention is not restricted to the above-mentioned ones.

As the cationic surface active agents, use may be made of Cotamine 24P(lauryltrimethylammonium chloride, Kao Atlas Co., Ltd., trade name), Cotamine 86P(stearyltrimethylammonium chloride, Kao Atlas Co., Ltd., trade name), Levasorp NL(laurylpyridinium bromide, Miyoshi Yushi Co., Ltd., trade name) and so on, but the present invention is not restricted to the above-mentioned ones.

As the amphoteric surface active agents, use may be made of Anhitol 24B(laurylbetaine, Kao Atlas Co., Ltd., trade name), Anhitol 86B(stearylbetaine, Kao Atlas Co., Ltd.,) and so on, but the present invention is not restricted to the above-mentioned ones.

Although the effective concentration of the surface active agent in the present invention is not specifically restricted, 0.01-20.0% is preferred.

2-pyridylazoaminophenol derivative or the salt thereof as a coloring reagent has a partial structure as a chromophore:

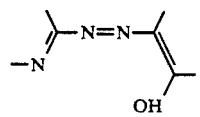

Typical compounds are included within 2-pyridylazoaminophenol derivative represented by the general formula (I) and the salt thereof.

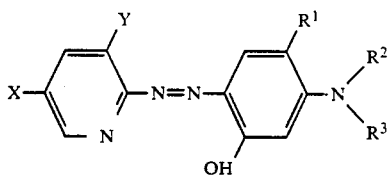

(I)

wherein X, Y represents a halogen atom or a hydrogen atom, $R^1$ represents a hydrogen atom or a lower alkyl group, $R^2$ and $R^3$ represent a hydrogen atom, a lower alkyl group, $-(CH_2)_nSO_3H$ in which n is an integer of 1-4, or

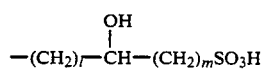

(l is an integer of 0-4, and m is an integer of 0-4. For instance, mention may be made of:

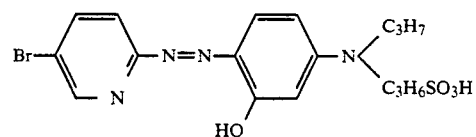
(1)

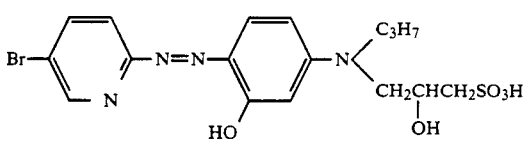
(2)

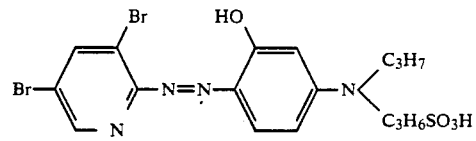
(3)

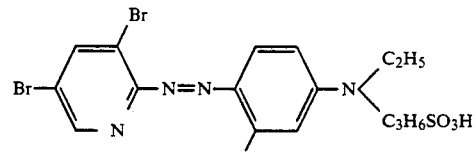
(4)

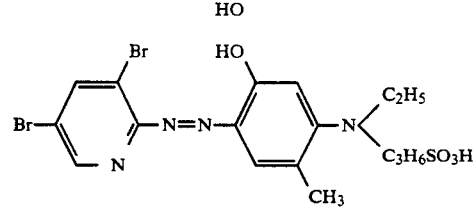
(5)

Among a series of compounds which are described as or a similar to a group of compounds disclosed in Japanese Patent Application No. 91,975/1982, the compounds in which the ortho position to an azo group of a benzene ring is substituted by a carboxyl group or an amino group are not necessarily satisfactory for the method of the present invention, and the substituting group should be a hydroxy group. In the case that X and Y of the general formula (I) are halogen atoms, the compounds are most easily synthesized when the halogen atoms are bromine atoms, and when they are chlorine, the synthesis is easier next to the former case. Similarly, the number of carbons in the lower alkyl group of $R^1$, $R^2$ and $R^3$ is practically 1-4. In an embodiment of the present invention, the salt of the coloring reagent of the general formula (I) is used, the salt an organic amine salt such as diethyl amine salt, triethylamine salt and the like, an inorganic salt such as ammonium salt, alkali metal salt, alkaline earth metal salt, and the like. The reason why these salts are used is mainly for the purpose of masking the coloring reagent of the present invention soluble in water. Among the coloring reagents according to the present invention, it is obvious that the compounds disclosed in Japanese Patent Application Laid-Open No. 91,975/1982, that is, the compounds of the general formula (I) in which at least one of $R^2$ and $R^3$ has a sulfonic acid group are soluble in water even when they are not converted into salts thereof. However, when the surface active agent is used in combination as in the case of the method of the present invention, the coloring reagents of the compounds of the general formula (I) themselves are not always required to be made soluble in water.

The present inventors have expended substantial efforts in further studies to look for the methods of miroanalysis which are specific to zinc and are high in sensitivity, and as a result they have found that when dimethylglyoxime which has conventionally been used as a coloring reagent of nickel is used together with the coloring reagent of the invention and the surface active agent, dimethylglyoxime surprisingly becomes an effective masking agent of nickel and cobalt. Based on this finding, the present inventors have accomplished the novel and useful method of the invention in which the compound which had not been used as the masking agent in the conventional analysis method is used as the masking agent of nickel and cobalt.

That is, the present invention relates to a method of colorimetrically measuring zinc in which one or more kinds of the surface active agents are used together with 2-pyridylazoaminophenol derivative or the salt thereof as a coloring reagent, and dimethylglyoxime is used as a masking agent of nickel and/or cobalt.

Dimethylglyoxime used in the present invention which is a masking agent of nickel and/or cobalt is generally used in a free form or disodium salt or in a mixed form thereof depending on the case, and may be used in a coloring reagent solution ordinarily at the concentration of 0.005-1.0%, preferably at the concentration of 0.01-0.5%.

On the other hand, appropriate use amounts of the masking agents of other metals are determined depending upon the masking effect, the influence thereof upon zinc, the solubility and so forth. For instance, when salicylaldoxime is used as the masking agent of copper, it is used ordinarily at the concentration of 0.005-0.5%, preferably at the concentration of 0.01-0.3%. When a citric acid salt is used as the masking agent of iron, it is used ordinarily at the concentration of 1.0-8.0%, preferably at the concentration of 2.0-5.0%.

As specific examples of the surface active agents and 2-pyridylazoaminophenol derivative or the salt thereof used in the present invention, the compounds exemplified in the first aspect of the present invention are used preferably too. The addition amount of these compounds are the same as mentioned above.

According to the method of the present invention, when a sample is serum, protein is removed therefrom, and then the sample is added to a reagent of the present invention in which the respectively appropriate amounts of the surface active agent and the coloring reagent are dissolved into a buffer aqueous solution of a given pH, or a reagent of the second aspect of the present invention in which an appropriate amount of dimethylglyoxime is dissolved into the former reagent, and the thus obtained solution is allowed to be left for a short time, for example, 5 minutes or 10 minutes. Thereafter, absorbance is measured at 555 nm with reference to a reagent blank as control, and the concentration of zinc in the sample is determined from comparison with a calibration curve.

The method of the present invention will be explained below with reference to the following example, which are merely illustrative of the invention, and never interpreted to limit the scope thereof.

EXAMPLE 1

Reagents (1) Coloring reagent solution 0.05 mM of each of five kinds of coloring reagents was dissolved into 600 ml of 0.05 M boric acid buffer solution of pH 8.5, to which Brij-35, sodium laurylbenzene sulfonate or Sundet ENM was added in an amount of 1.6%, and dilution was made with water to be 1 liter in a total volume.

(2) Sample solution A 14 mg (5 mg when calculated as zinc) of zinc acetate was dissolved into water to be 1 liter in a total volume.

(3) Sample solution B 48 mg (10 mg when calculated as iron) of ammonium iron (III) sulfate was dissolved into 0.1 N-HCl to be 100 ml in a total volume.

(4) Sample solution C 18 mg (5 mg when calculated as copper) of copper sulfate was dissolved into water to be 100 ml in a total volume.

(5) Sample solution D 11 mg (5 mg when calculated as nickel) of nickel chloride was dissolved into water to be 100 ml in a total volume.

(6) Sample solution E 11 mg (5 mg when calculated as cobalt) of cobalt chloride was dissolved into water to be 100 ml in a total volume.

Test method 3 ml of the coloring reagent solution was added to 20 μl of each of Sample solutions A-E, which was allowed to be left at room temperature for 20 minutes. Thereafter, absorbance was measured at 555 nm with reference to a reagent blank as control.

In Table 1 are shown differences in coloring degree among the coloring reagents with the respective metal ions depending upon the presence or the absence of the surface active agents. The coloring degrees of the respective metals are changed by the addition of the surface active agents, and particularly the coloring degree of Fe is lowered to about one fourth when Brij-35 was added, thereby relatively enhance the specificity of zinc.

TABLE 1

| Coloring reagent | Surface active agent | Zn 5 mg/dl | Cu II 5 mg/dl | Fe III 10 mg/dl | Ni II 5 mg/dl | Co III 5 mg/dl | 555 nm OD |
|---|---|---|---|---|---|---|---|
| 5Br-PAPS (structure: Br-pyridyl-N=N-phenyl(HO)-N(C$_3$H$_7$)(C$_3$H$_6$SO$_3$H)) | No | 0.826 | 0.671 | 0.195 | 0.940 | 0.582 | |
| | Brij-35 | 0.760 | 0.641 | 0.052 | 0.613 | 0.526 | |
| | SLS | 0.813 | 0.522 | 0.086 | 0.780 | 0.531 | |
| | Sundet ENM | 0.616 | 0.581 | 0.281 | 0.730 | 0.506 | |
| Br-pyridyl-N=N-phenyl(HO)-N(C$_3$H$_7$)(CH$_2$CHCH$_2$SO$_3$H with OH) | No | 0.621 | 0.646 | 0.173 | 0.795 | 0.529 | |
| | Brij-35 | 0.571 | 0.616 | 0.046 | 0.518 | 0.478 | |
| | SLS | 0.614 | 0.502 | 0.076 | 0.660 | 0.482 | |
| | Sundet ENM | 0.459 | 0.559 | 0.249 | 0.617 | 0.460 | |
| Br, Br-pyridyl-N=N-phenyl(HO)-N(C$_3$H$_7$)(C$_3$H$_6$SO$_3$H) | No | 0.601 | 0.675 | 0.143 | 0.829 | 0.493 | Every figure shows the absorbance at 555 nm |
| | Brij-35 | 0.563 | 0.622 | 0.038 | 0.541 | 0.445 | |
| | SLS | 0.592 | 0.532 | 0.063 | 0.688 | 0.450 | |
| | Sundet ENM | 0.432 | 0.509 | 0.201 | 0.641 | 0.429 | |
| Br, Br-pyridyl-N=N-phenyl(HO)-N(C$_2$H$_5$)(C$_3$H$_6$SO$_3$H) | No | 0.677 | 0.562 | 0.187 | 0.830 | 0.564 | |
| | Brij-35 | 0.613 | 0.537 | 0.049 | 0.540 | 0.510 | |
| | SLS | 0.666 | 0.437 | 0.083 | 0.688 | 0.515 | |
| | Sundet ENM | 0.565 | 0.486 | 0.270 | 0.644 | 0.491 | |
| Br, Br-pyridyl-N=N-phenyl(HO, CH$_3$)-N(C$_2$H$_5$)(C$_3$H$_6$SO$_3$H) | No | 0.459 | 0.596 | 0.080 | 0.433 | 0.469 | |
| | Brij-35 | 0.422 | 0.569 | 0.021 | 0.320 | 0.424 | |
| | SLS | 0.452 | 0.463 | 0.035 | 0.407 | 0.428 | |
| | Sundet ENM | 0.343 | 0.516 | 0.115 | 0.381 | 0.408 | |

TABLE 1-continued

| Coloring reagent | Surface active agent | Zn 5 mg/dl | Cu II 5 mg/dl | Fe III 10 mg/dl | Ni II 5 mg/dl | Co III 5 mg/dl | 555 nm OD |
|---|---|---|---|---|---|---|---|

REFERENCE EXAMPLE 1

Reagents (1) Coloring reagent solution 0.05 mmol of 5-Br-PAPS{2-(5-bromo-2-pyridylazo)-5-(N-propyl-N-sulfopropylamino)phenol sodium salt}, 33 g of sodium citrate, 1 g of salicyclaldoxime and 0.03 mol of borax were dissolved into water to be 1 liter in a total volume, and the pH was adjusted to 9.5 with hydrochloric acid.

(2) Sample solution A
Same as Example 1
(3) Sample solution B
Same as Example 1
(4) Sample solution C
Same as Example 1
(5) Sample solution D
Same as Example 1
(6) Sample solution E
Same as Example 1

Test method 3 ml of the coloring reagent solution was added to 20 μl of each of Sample solutions A-E, which was allowed to be left at room temperature for 20 minutes. Thereafter, absorbance was measured at 555 nm with reference to a reagent blank as control.

In Table 2 are shown absorbances of the respective metals and relative values of the metals when the coloring degree of zinc is taken as 100.

TABLE 2

|  | Zn | Fe | Cu | Ni | Co |
|---|---|---|---|---|---|
| Absorbance | 0.726 | 0.091 | 0.027 | 0.832 | 0.461 |
| Relative value when the Coloring degree of Zinc is taken as 100 | 100 | 13 | 4 | 115 | 63 |

EXAMPLE 2

Reagents (1) Coloring reagent solution 0.05 mmol of 5Br-PAPS, 33 g of sodium citrate, 1 g of salicylaldoxime, 0.03 mol of borax, and the following surface active agent were dissolved into water to be 1 liter in a total volume, and the pH was adjusted to 9.5 with hydrochloric acid.

As the surface active agent, Triton X-100, Brij-35, Emulgen 120, Tween 20, Tween 80, Softanol 90, Emusol 3130, Anhytol 24B, Cotamine 24P, Cotamine 86P, Levenol WX, sodium laurylsulfate, or Demol N was singly used in an amount of 1.6%. Alternatively, Brij-35 and Triton X-100 were used together each at an amount of 1%, or sodium laurylsulfate and Demol N were used together each at an amount of 1%. (In the above, the respective percentages of the ingredients are expressed with respect to the weight of the whole coloring reagent solution.)

(2) Sample solution A
Sample as Example 1
(3) Sample solution B
Same as Example 1
(4) Sample solution C
Same as Example 1
(5) Sample solution D
Same as Example 1
(6) Sample solution E
Same as Example 1

Test method 3 ml of each of the coloring reagent solutions containing the respective surface active agents was added to 20 μl of Sample solutions A-E, which was allowed to be left at room temperature for 20 minutes. Thereafter, absorption was measured at 555 nm with reference to a reagent blank as control.

In Table 3 are shown the coloring percentages of the respective metals with respect to those in Reference Example 1, and the relative values of the metals when the coloring degree of zinc was taken as 100.

TABLE 3

| Surface active agent | | Coloring percentage | | | | |
|---|---|---|---|---|---|---|
| Classification | Trade name | Zn 5 mg/dl | Fe 10 mg/dl | Cu 5 mg/dl | Ni 5 mg/dl | Co 5 mg/dl |
| Nonionic type | Triton X-100 | 109% | 36% | 93% | 47% | 63% |
|  |  | 100 | 4 | 3 | 50 | 36 |
|  | Brig-35 | 107% | 13% | 7% | 58% | 36% |
|  |  | 100 | 2 | 0 | 62 | 21 |
|  | Emulgen 120 | 94% | 24% | 39% | 40% | 72% |
|  |  | 100 | 3 | 2 | 49 | 48 |
|  | Tween 20 | 125% | 76% | 31% | 57% | 63% |
|  |  | 100 | 8 | 1 | 52 | 32 |
|  | Tween 80 | 105% | 10% | 41% | 61% | 60% |
|  |  | 100 | 1 | 2 | 67 | 36 |
|  | Softanol 90 | 101% | 23% | 70% | 51% | 62% |
|  |  | 100 | 3 | 3 | 50 | 39 |
|  | Emusol 3130 | 93% | 19% | 0% | 72% | 59% |
|  |  | 100 | 3 | 0 | 89 | 40 |
|  | Brij-35 Triton X-100 | 109% | 25% | 64% | 45% | 35% |
|  |  | 100 | 3 | 2 | 48 | 20 |
| Amphoteric | Anhytol | 81% | 6% | 0% | 42% | 60% |

TABLE 3-continued

| Surface active agent | | Coloring percentage | | | | |
|---|---|---|---|---|---|---|
| Classification | Trade name | Zn 5 mg/dl | Fe 10 mg/dl | Cu 5 mg/dl | Ni 5 mg/dl | Co 5 mg/dl |
| type | 24B | 100 | 1 | 0 | 60 | 47 |
| Cationic | Cotamine | 84% | 21% | 17% | 39% | 55% |
| type | 24P | 100 | 3 | 1 | 53 | 41 |
| | Cotamine | 67% | 19% | 0% | 27% | 50% |
| | 86P | 100 | 4 | 0 | 46 | 47 |
| Anionic | Levenol | 101% | 9% | 51% | 68% | 63% |
| type | WX | 100 | 1 | 2 | 77 | 39 |
| | Sodium lauryl | 102% | 27% | 0% | 54% | 58% |
| | sulfate | 100 | 3 | 0 | 61 | 36 |
| | Demol N | 88% | 12% | 24% | 31% | 35% |
| | | 100 | 2 | 1 | 41 | 25 |
| | Sodium lauryl | 102% | 15% | 7% | 45% | 40% |
| | sulfate | | | | | |
| | Demol N | 100 | 2 | 1 | 51 | 25 |

(In the upper lines of the column of "Coloring percentage" are given the coloring percentages of the respective metals with respect to the coloring-percentages in Reference Example 1, whereas in the lower lines are given the relative values of the metals when the coloring degrees of zinc is taken as 100).

As obvious from Tables 2 and 3, the specificity to zinc is enhanced by the addition of the surface active agents. In particular, the method of the present invention is excellent in inhibit of the coloring of iron and copper.

For instance, even when citric acid and salicylaldoxime are coexistent, the coloring degree of iron is 13 provided that iron is added in an amount of twice by weight as large as that of each of the other metal, and that of copper is 4, while the coloring degree of zinc is 100. To the contrary, when Brij-35, Emulgen 120, Tween 80, Emusol 3130, sodium lauryl sulfate (SLS), Levenol WX, Demol N, Cotamine 24P, or Anhytrol 24B was added in an amount of 1.6%, the coloring degree of iron J-3, and that of copper is 0-2, while the coloring degree of zinc is 100. Thus, the specificity to zinc is overwhelmingly enhanced. Since no practical problems rise in the clinically chemical analysis when the coloring of iron and copper is inhibited, this is extremely important effect.

EXAMPLE 3

Reagents (1) Coloring reagent solution 0.05 mmol of 5Br-PAPS, 33 g of sodium citrate, 1 g of salicylaldoxime, Alanon ACE in an amount of 1.6% or Alanon ACE in an amount of 0.7% and Brij-35 in an amount of 1% as surface active agent, and 0.03 mol of borax were dissolved into water to be 1 liter in a total volume, and the pH was adjusted to 9.5 with hydrochloric acid. (In the above, the respective percentages of the ingredients are expressed with respect to the weight of the whole coloring reagent solution.)

(2) Sample solution A
Same as Example 1
(3) Sample solution B
Same as Example 1
(4) Sample solution C
Same as Example 1
(5) Sample solution D
Same as Example 1
(6) Sample solution E
Same as Example 1

Test method 3 ml of each of the coloring reagent solutions containing the respective surface active agents was added to 20 µl of every one of Sample solutions A-E, which was allowed to be left at room temperature for 20 minutes. Thereafter, absorbance was measured at 555 nm with reference to a reagent blank.

In Table 4 are shown the coloring percentages of the respective metals with respect to those in Reference Example 1, and the relative values of the metals when the coloring degree of zinc is taken as 100.

TABLE 4

| Surface active agent | | Coloring percentage | | | | |
|---|---|---|---|---|---|---|
| Anionic type | Nonionic type | Zn | Fe | Cu | Ni | Co |
| Alanon ACE | — | 1% | 9% | 121% | 57% | 8% |
| | | — | — | — | — | — |
| Alanon ACE (0.7%) | Brig-35 (1%) | 90% 100 | 15% 2 | 100% 4 | 18% 23 | 0% 0 |

(In the upper lines of the column "Coloring percentage" are shown the coloring percentages of the respective metals with respect to the coloring percentages in Reference Example 1, whereas in the lower lines are given the relative values of the respective metals when the coloring degree of zinc is taken as 100).

As obvious from Table 4, the coloring percentage of zinc is 0-1% when the anionic surface active agent was used singly, when the nonionic surface active agent is coexistent, zinc is removed form from masking and cobalt is further masked.

As explained in the foregoing, when the surface active agents are appropriately selected and used in combination noting an interfering metal which is anticipated to be present in a sample, zinc can be quantitatively measured with accuracy.

EXAMPLE 4

Reagents (1) Coloring reagent solution 0.05 ml of 5Br-PAPS, 33 g sodium citrate, 1 g of salicylaldoxime, 0.03 mol of borax, and 10 g of Brij-35 were dissolved into water to be 1 liter in a total volume, and the pH was adjusted to 9.5 with hydrochloric acid.

(2) Sample solution

Sample solution presumed to contain about 100 µg/dl of zinc Measuring method:

3 ml of the coloring reagent solution was added to 1 ml of the sample solution, which was allowed to be left at room temperature for 5 minutes. Thereafter, absorbance was measured at 555 nm with reference to a reagent blank as control to determine the concentration of zinc.

As obvious from Tables 2 and 3, the influence of iron is lowered to about one sixth at this case as compared with the case where no Brij-35 was added.

EXAMPLE 5

Reagents (1) Coloring reagent solution 0.05 mmol of 5Br-PAPS, 33 g of sodium citrate, 1 g of salicylaldoxime, 20 g of Brij-35, and 20 g of Triton X-100 were dissolved into 0.05 M carbonate buffer solution to be 1 liter in a total volume, and its pH was adjusted to 9.5 with a hydrochloric acid.

(2) Sample solution

Serum (3) EDTA.tetrasodium salt solution

1 M EDTA.tetrasodium salt solution was prepared.

Measuring method 2.5 ml of the coloring reagent solution was added to 200 µl of the sample solution, which was allowed to be left at room temperature for 5 minutes. Thereafter, absorbance was measured at 555 nm. Then, a drop of the EDTA-tetrasodium salt solution was added for decoloring the solution, which was allowed to be left for 10 minutes. Subsequently, a sample blank was obtained by measuring absorbance at 555 nm through using the solution added with EDTA as control. The concentration of zinc was determined by subtracting the absorbance of the sample blank from that of the sample.

At this time, as obvious from Table 3, substantially no influence was observed even when iron or copper was present.

EXAMPLE 6

Reagents (1) Coloring reagent solution 0.05 mmol of 5 Br-PAPS, 33 g of sodium citrate, 1 g of salicylaldoxime, 16 g of Emusol 3130 and 0.03 mol of borax were dissolved into water to be 1 liter, and the pH was adjusted to 9.5 with hydrochloric acid.

(2) Sample solution

Same as Example 4

Measuring method 3 ml of the coloring reagent solution was added to 1 ml of the sample solution, which was allowed to be left at room temperature for 5 minutes. Thereafter, the absorbance was measured at 555 nm with reference to a reagent blank as control, and the concentration of zinc was determined therefrom.

At this time, as obvious from Table 3, substantially no influence was observed even when iron or copper was present.

EXAMPLE 7

Reagents (1) Coloring reagent solution 0.05 mmol of 5Br-PAPS, 1 g of salicylaldoxime, 7 g of Alanon ACE, 10 g of Brij-35, and 0.03 mol of borax were dissolved into water to be 1 liter in a total volume, and the pH was adjusted to 9.5 with hydrochloric acid.

(2) Sample solution

Same as Example 4

Measuring method 3 ml of the coloring reagent was added to 1.0 ml of the sample solution, which was allowed to be left at room temperature for 5 minutes. Thereafter, absorbance was measured at 555 nm with reference to a reagent blank as control, and the concentration of zinc was determined therefrom.

At this time, as obvious from Table 4, no interference was seen even when cobalt was coexistenced.

EXAMPLE 8

Reagents (1) Coloring reagent solution 0.05 mmol of 5Br-PAPS, 33 g of sodium citrate, 1 g of salicylaldoxime, 16 g of Levenol WX and 0.03 mol of borax were dissolved into water to be 1 liter in a total volume, and the pH was adjusted to 9.5 with hydrochloric acid.

(2) Sample solution

Same as Example 4

Measuring method 3 ml of the coloring reagent solution was added to 1 ml of the sample solution, which was allowed to be left at room temperature for 5 minutes. Thereafter, absorbance was measured at 555 nm with reference to a reagent blank as control, and the concentration of zinc was determined therefrom.

At this time, as obvious from Table 3, substantially no influence was observed even when iron or copper was present.

EXAMPLE 9

Reagent (1) Coloring reagent solution 0.05 mmol of 5 Br-PAPS, 33 g of sodium citrate, 1 g of salicylaldoxime, 10 g of sodium laurylsulfate, 10 g of Demol N, and 0.03 mol of borax was dissolved into water to be 1 liter in a total volume, and the pH was adjusted to 95 with hydrochloric acid.

(2) Sample solution

Same as Example 4

Measuring method 3 ml of the coloring reagent solution was added to 1 ml of the sample solution, which was allowed to be left at room temperature for 5 minutes. Thereafter, absorbance was measured at 555 nm with reference to a reagent blank as control, and the concentration of zinc was determined therefrom.

At that time, as obvious from Table 3, substantially no interference in the measurement was observed even when iron or copper was present.

EXAMPLE 10

Reagents (1) Coloring reagent solution 0.05 mM of 5 Br-PAPS 33 g of sodium citrate, 1 g of salicylaldoxime, 1.0 g of dimethylglyoxime, and the following surface active agent were dissolved into 1 liter of 0.05 M carbonate buffer solution of pH 9.5.

As the surface active agent, 40 g of Triton X-100 or 40 g of Brij-35 was singly used. Alternatively, 40 g of Triton X-100 and 40 g of Brij-35 were used in combination or no surface active agent was added.

(2) Sample solution A 14 mg (5 mg when calculated as zinc) of zinc acetate was dissolved into water to be 100 ml in a total volume.

(3) Sample solution B 25 mg (5 mg when calculated as iron) of ammonium iron (II) sulfate was dissolved into 0.1 N-HCl to be 100 ml in a total volume.

(4) Sample solution C 24 mg (5 mg when calculated as iron) of ammonium iron (III) sulfate was dissolved into 0.1 N-HCl to be 100 ml of in a total volume.

(5) Sample solution D 18 mg (5 mg when calculated as copper) of copper sulfate was dissolved into water to be 100 ml in a total volume.

(6) Sample solution E 11 mg (5 mg when calculated as nickel) of nickel chloride was dissolved into water to be 100 ml in a total volume.

(7) Sample solution F 11 mg (5 mg when calculated as cobalt) of cobalt chloride was dissolved into water to be 100 ml in a total volume.

Experimental Method 3 ml of the coloring reagent solution containing the surface active agent or no surface active agent was added to 20 μl of each of Sample solutions A–F, which was allowed to be left at room temperature for 20 minutes. Thereafter, absorbance was measured at 555 nm with reference to a reagent blank as control. Results are shown in Table 5.

TABLE 5

| Surface active agent | Coloring degree | | | | | |
|---|---|---|---|---|---|---|
| | Zn | FeII | FeIII | Cu | Ni | Co |
| No addition | 0.732 | 0.111 | 0.097 | 0.015 | 0.476 | 0.009 |
| | 100.0 | 15.2 | 13.3 | 2.0 | 65.0 | 1.2 |
| Brig-35 | 0.763 | 0.014 | 0.006 | 0.001 | 0.026 | 0.001 |
| | 100.0 | 1.8 | 0.7 | 0.1 | 3.4 | 0.1 |
| Triton X-100 | 0.759 | 0.010 | 0.002 | 0.003 | 0.021 | 0.003 |
| | 100.0 | 1.3 | 0.3 | 0.4 | 2.8 | 0.4 |
| Brig-35 | 0.762 | 0.004 | 0.000 | 0.000 | 0.008 | 0.001 |
| Triton X-100 | 100.0 | 0.5 | 0.0 | 0.0 | 1.0 | 0.1 |

(The above lines in the column "Coloring degree" give the absorbances of the respective metals, where as the lower lines give the relative values of the metals when the coloring degree of zinc is taken as 100).

Further, in Table 6 are shown results on the coloring degrees of the respective metals similarly measured when neither surface active agent nor the masking agent according to the present invention were added and results on the coloring degrees of the respective metals similarly measured when Brij-35, and Triton X-100 were used in combination without the masking agent of the present invention (dimethylglyoxime). At this time, 48 mg (10 mg when calculated as iron) of ammonium iron (III) sulfate which was dissolved in 0.1 N-HCl to be 100 ml in a total volume was used instead of Sample solution B or Sample solution C.

TABLE 6

| | Coloring degree | | | | |
|---|---|---|---|---|---|
| | Zn | FeIII | Cu | Ni | Co |
| Neither surface active agent nor dimethylglyoxime added | 0.726 100.0 | 0.091 13 | 0.027 4 | 0.832 115 | 0.461 63 |

TABLE 6-continued

| | Coloring degree | | | | |
|---|---|---|---|---|---|
| | Zn | FeIII | Cu | Ni | Co |
| No dimethylglyoxime added | 0.791 | 0.023 | 0.017 | 0.374 | 0.161 |
| Surface active agent added | 100.0 | 2.9 | 2.1 | 47.3 | 20.4 |

(The upper lines in the column "Coloring degree" show the absorbances of the respective metals, whereas the lower lines show the relative values of the metals when the coloring degree of zinc is taken as 100).

As obvious from Tables 5 and 6, the quantitative measurement of zinc can be accurately performed by appropriately selecting and combining using dimethylglyoxime, the conventionally used masking agent and the surface active agents.

EXAMPLE 11

Reagents (1) Coloring reagent solution 0.05 mmol of 5Br-PAPS, 33 g of sodium citrate, 1 g of salicylaldoxime, 1 g of dimethylglyoxime, 40 g of Brij-35 and 40 g of Triton X-100 were dissolved into 0.05 M carbonate buffer solution to be 1 liter in a total volume, and the pH was adjusted to 9.5 with hydrochloric acid.

(2) Sample solution

Serum (3) EDTA.tetrasodium salt solution

1 M EDTA.tetrasodium salt solution was prepared.

Measuring method 2.5 of the coloring reagent solution was added to 200 μl of the sample solution, which was allowed to be left at room temperature for 5 minutes. Thereafter, absorbance was measured at 555 nm with reference to a reagent blank as control. A drop of 1 M EDTA solution was added to this coloring reagent solution, which was allowed to be left for 5 minutes after stirring. Then, absorbance was measured again at 555 nm with reference to a reagent blank to which EDTA was added as control, and the concentration of zinc was determined by subtracting a sample blank therefrom.

Results are shown in Table 7 while being compared with those according to the atomic absorption method.

TABLE 7

| No. | Method of invention (μg/dl) | Atomic absorption method (μg/dl) | No. | Method of invention (μg/dl) | Atomic absorption method (μg/dl) |
|---|---|---|---|---|---|
| 1 | 108 | 106 | 22 | 97 | 100 |
| 2 | 86 | 94 | 23 | 81 | 85 |
| 3 | 63 | 63 | 24 | 85 | 88 |
| 4 | 64 | 63 | 25 | 75 | 75 |
| 5 | 75 | 75 | 26 | 112 | 106 |
| 6 | 66 | 56 | 27 | 44 | 38 |
| 7 | 106 | 106 | 28 | 84 | 81 |
| 8 | 80 | 81 | 29 | 90 | 85 |
| 9 | 76 | 75 | 30 | 80 | 75 |
| 10 | 89 | 88 | 31 | 86 | 75 |
| 11 | 88 | 85 | 32 | 104 | 113 |
| 12 | 93 | 94 | 33 | 63 | 63 |
| 13 | 77 | 75 | 34 | 95 | 94 |
| 14 | 106 | 106 | 35 | 74 | 75 |
| 15 | 91 | 94 | 36 | 80 | 81 |
| 16 | 63 | 63 | 37 | 108 | 106 |
| 17 | 77 | 85 | 38 | 75 | 63 |
| 18 | 61 | 63 | 39 | 97 | 94 |
| 19 | 89 | 88 | 40 | 78 | 81 |
| 20 | 83 | 82 | average | 83.175 | 82.363 |

| No. | Method of invention (μg/dl) | Atomic absorption method (μg/dl) | No. | Method of invention (μg/dl) | Atomic absorption method (μg/dl) |
|---|---|---|---|---|---|
| 21 | 78 | 75 | | | |

As obvious from Table 7, the method according to the present invention and the atomic absorption method are well in conformity with each other at a relation coefficient of 0.962.

What is claimed is:

1. A method for a colorimetric determination of zinc in serum from living organisms consisting essentially of steps:
   a) preparing a coloring reagent for zinc comprising
      1) an aqueous soluble 2-pyridylazo-aminophenol derivative or a salt of a 2-pyridylazoamino-phenol derivative, represented by the formula (I):

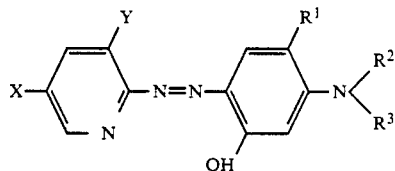

wherein:
X and Y represent a member from the group consisting of a halogen atom and a hydrogen atom,
$R^1$ is selected from the group consisting of a hydrogen atom and a lower alkyl group, and
$R^2$ and $R^3$ are selected from the group consisting of a hydrogen atom, a lower alkyl group, —(CH$_2$)$_n$SO$_3$H in which n is an integer from 1-4, and

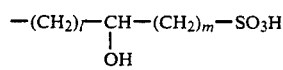

in which l is an integer from 0-4 and m is an integer from 0-4, wherein at least one of $R^2$ and $R^3$ is —(CH$_2$)$_n$SO$_3$H or

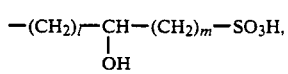

and
   2) a mixture comprising at least one surface active agent, salicylaldoxime and dimethylglyoxime, which mixture is capable of masking a metal selected from the group consisting of Ni, Co, Fe, and Cu;
   b) adding the coloring reagent solution to a sample solution containing zinc; and
   c) measuring the absorbance of the solution at 555 nm.

2. The method according to claim 1, wherein $R^3$ is —(CH$_2$)$_n$—SO$_3$H wherein n is an integer from 1-4.

3. The method according to claim 1, wherein $R^2$ is —(CH$_2$)$_n$—SO$_3$H wherein n is an integer from 1-4.

4. The method according to claim 1 wherein $R^3$ is

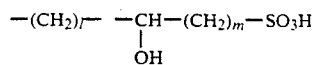

wherein l is an integer greater than 0 and m is an integer greater than 0.

5. The method according to claim 1, wherein $R^2$ and $R^3$ are either (I) —(CH$_2$)$_n$—SO$_3$H in which n is an integer from 1-4 or (II)

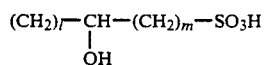

in which l is an integer from 0-4 and m is an integer from 0-4.

6. A composition for the colorimetric determination of zinc in serum from living organisms consisting essentially of:
   a) an aqueous soluble 2-pyridylazoaminophenol derivative or a salt of a 2-pyridylazoaminophenol derivative, represented by the following formula (I):

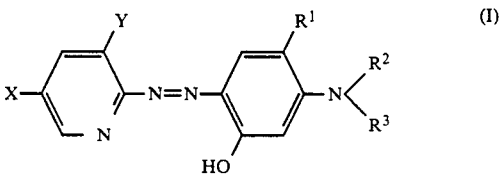

wherein:
X and Y represent a member of the group consisting of a halogen atom and a hydrogen atom,
$R^1$ is selected from the group consisting of a hydrogen atom and a lower alkyl group, and
$R^2$ and $R^3$ are selected from the group consisting of a hydrogen atom, a lower alkyl group, —(CH$_2$)$_n$SO$_3$H in which n is an integer from 1-4, and

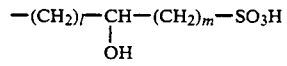

in which l is an integer from 0-4 and m is an integer from 0-4, wherein at least one of $R^2$ and $R^3$ is —(CH$_2$)$_n$SO$_3$H or

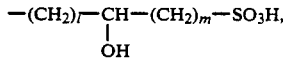

as a coloring reagent for zinc, and
   b) a mixture comprising at least one surface active agent, salicylaldoxime and dimethylglyoxime, which mixture is capable of masking a metal selected from the group consisting of Ni, Co, Fe, and Cu.

7. A composition according to claim 6, wherein $R^1$ is a lower alkyl group having from 1 to 4 carbon atoms.

8. A composition according to claim 6, wherein $R^2$ and $R^3$ represent, a lower alkyl group having from 1 to 4 carbon atoms.

9. A composition according to claim 6, wherein X and Y represent, independently of one another, a member selected group a group consisting of bromine, chlorine, and hydrogen.

10. A composition according to claim 6, wherein the pyridylazoaminophenol derivative or a salt thereof is selected from the group consisting of:

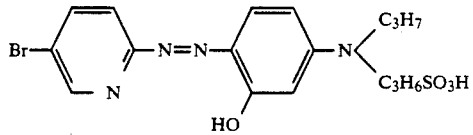

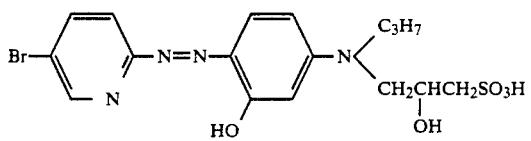

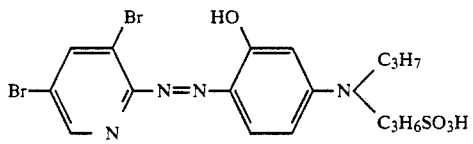

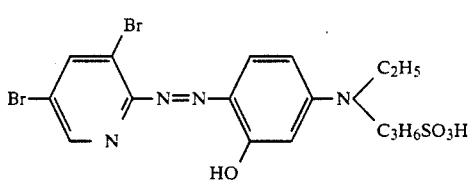

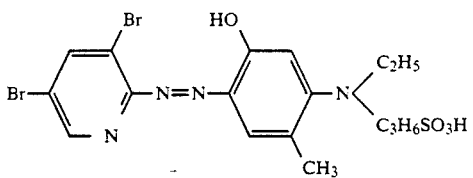

and salts thereof.

11. The composition according to claim 6, wherein $R^3$ is $-(CH_2)_n-SO_3H$ and n is an integer from 1-4.

12. The composition according to claim 6, wherein $R^2$ is $-(CH_2)_n-SO_3H$ and n is an integer from 1-4.

13. The composition according to claim 6, wherein $R^3$ is

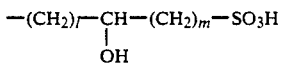

and l is an integer from 0-4 and m is an integer from 0-4.

14. The composition according to claim 6, wherein $R^2$ and $R^3$ are either (I) $-(CH_2)_n-SO_3H$ in which n is an integer from 1-4 or (II)

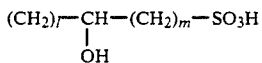

in which l is an integer from 0-4 and m is an integer from 0-4.

* * * * *